United States Patent
Frushour

(10) Patent No.: US 9,943,358 B2
(45) Date of Patent: Apr. 17, 2018

(54) METHOD FOR FERROMAGNETIC CLAMPING AND CUTTING IN A PORTABLE MEDICAL DEVICE

(71) Applicant: COVIDIEN LP, Mansfield, MA (US)

(72) Inventor: Scott E. M. Frushour, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 571 days.

(21) Appl. No.: 14/601,762

(22) Filed: Jan. 21, 2015

(65) Prior Publication Data
US 2015/0351827 A1 Dec. 10, 2015

Related U.S. Application Data

(60) Provisional application No. 62/009,429, filed on Jun. 9, 2014.

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/1455* (2013.01)

(58) Field of Classification Search
CPC ............... A61B 17/285; A61B 17/295; A61B 2017/2902; A61B 2017/2912; A61B 2017/2932; A61B 2017/320028; A61B 18/1442; A61B 18/1445; A61B 2018/1455; A61B 5/15115; A61B 5/15123

See application file for complete search history.

(56) References Cited

U.S. PATENT DOCUMENTS

| | | |
|---|---|---|
| 3,874,372 A | 4/1975 | Le Bon |
| 5,047,046 A | 9/1991 | Bodoia |
| 5,601,601 A | 2/1997 | Tal et al. |
| 5,807,393 A | 9/1998 | Williamson, IV et al. |
| 6,458,130 B1 | 10/2002 | Frazier et al. |
| 6,684,681 B1 | 2/2004 | Zombo |
| 6,740,079 B1 | 5/2004 | Eggers et al. |
| 7,967,839 B2 | 6/2011 | Flock et al. |
| 8,157,145 B2 | 4/2012 | Shelton, IV et al. |
| 8,187,273 B2 * | 5/2012 | Kerr ............... A61B 18/1206 606/51 |
| 2004/0210282 A1 | 10/2004 | Flock et al. |
| 2005/0021078 A1 * | 1/2005 | Vleugels ............ A61B 17/29 606/205 |

(Continued)

*Primary Examiner* — Ronald Hupczey, Jr.

(57) ABSTRACT

The present disclosure relates to a surgical instrument including a housing, an elongated member, an end effector assembly, a drive assembly, a solenoid assembly, and a switch assembly. The end effector assembly is coupled to a distal end of the elongated member. The end effector assembly includes a first jaw member and an opposing second jaw member. The drive assembly is disposed within the elongated member and operably coupled to the end effector and configured to move the first jaw member from a first position to a second position. The solenoid assembly is disposed within the housing. The solenoid assembly is operably coupled to the drive assembly and adapted to connect to a power source. The switch assembly is activatable to energize the solenoid assembly such that the solenoid assembly actuates the drive assembly to move the first jaw member from the first position to the second position.

15 Claims, 6 Drawing Sheets

(56) References Cited

U.S. PATENT DOCUMENTS

| | | | |
|---|---|---|---|
| 2012/0116379 A1* | 5/2012 | Yates | A61B 17/00234 606/33 |
| 2012/0221004 A1 | 8/2012 | Kerr et al. | |
| 2012/0310111 A1* | 12/2012 | Shachar | A61B 5/06 600/567 |
| 2013/0270322 A1 | 10/2013 | Scheib et al. | |

* cited by examiner

METHOD FOR FERROMAGNETIC CLAMPING AND CUTTING IN A PORTABLE MEDICAL DEVICE

CROSS REFERENCE TO RELATED APPLICATION

The present application claims the benefit of and priority to U.S. Provisional Application Ser. No. 62/009,429, filed on Jun. 9, 2014, the entire contents of which are incorporated herein by reference.

BACKGROUND

The present disclosure relates to an electrosurgical forceps and more particularly, the present disclosure relates to a bipolar electrosurgical forceps for sealing and/or cutting tissue including one or more solenoids for actuating the forceps.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal the tissue.

As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time. By utilizing an electrosurgical forceps, a surgeon can cauterize, coagulate/desiccate, reduce or slow bleeding and/or seal vessels by controlling the intensity, frequency, and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

Conventional forceps utilize manual force to actuate jaw members and/or cutting mechanisms. Accordingly, there is a need to provide for powered actuation of the electrosurgical forceps.

SUMMARY

According to one embodiment of the present disclosure, a surgical instrument is provided. The surgical instrument includes a housing, an elongated member, an end effector assembly, a drive assembly, a solenoid assembly, and a switch assembly. The elongated member extends distally from the housing and defines a longitudinal axis. The end effector assembly is coupled to a distal end of the elongated member. The end effector assembly includes a first jaw member and an opposing second jaw member. The first jaw member is moveable relative to the second jaw member from a first position in spaced relation to the second jaw member to a second position closer to the second jaw member to grasp tissue therebetween. At least one of the first and second jaw members are adapted to connect to an electrosurgical energy source such that the first and second jaw members are capable of conducting the electrosurgical energy through tissue grasped therebetween to effect a tissue seal. The drive assembly is disposed within the elongated member and operably coupled to the end effector and configured to move the first jaw member from the first position to the second position. The solenoid assembly is disposed within the housing. The solenoid assembly is operably coupled to the drive assembly and adapted to connect to a power source. The switch assembly is connected to the housing. The switch assembly is activatable to energize the solenoid assembly such that the solenoid assembly actuates the drive assembly to move the first jaw member from the first position to the second position.

In one aspect, the surgical instrument further includes a selectively advanceable knife assembly along the longitudinal axis, wherein the knife assembly is disposed between the first jaw member and the second jaw member.

In one aspect, the solenoid assembly is configured to actuate the knife assembly, the knife assembly being movable after the first jaw member is actuated from the first position to the second position.

In one aspect, the switch assembly is configured to selectively supply electrosurgical energy to the first and second jaw members to effect the tissue seal.

In one aspect, the first jaw is configured to couple to a first electrical potential and the second jaw is configured to couple to a second electrical potential.

In one aspect, the drive assembly includes a reciprocating sleeve which, upon energization of the solenoid assembly, is moved along the longitudinal axis to move the first jaw member relative to the second jaw member.

In one aspect, the solenoid assembly includes at least one solenoid and is coupled with a ferromagnetic shaft of the drive assembly.

According to one embodiment of the present disclosure, a surgical system is provided. The surgical system includes an electrosurgical generator and a surgical instrument. The electrosurgical generator includes an RF output stage configured to generate electrosurgical energy. The surgical instrument includes a housing, an elongated member, an end effector assembly, a drive assembly, a solenoid assembly, and a switch assembly. The elongated member extends distally from the housing and defines a longitudinal axis. The end effector assembly is coupled to a distal end of the elongated member. The end effector assembly includes a first jaw member and an opposing second jaw member. The first jaw member is moveable relative to the second jaw member from a first position in spaced relation to the second jaw member to a second position closer to the second jaw member to grasp tissue therebetween. At least one of the first and second jaw members are adapted to connect to an electrosurgical energy source such that the first and second jaw members are capable of conducting the electrosurgical energy through tissue grasped therebetween to effect a tissue seal. The drive assembly is disposed within the elongated member and operably coupled to the end effector and configured to move the first jaw member from the first position to the second position. The solenoid assembly is disposed within the housing. The solenoid assembly is operably coupled to the drive assembly and adapted to connect to a power source. The switch assembly is connected to the housing. The switch assembly is activatable to energize the solenoid assembly such that the solenoid assembly actuates the drive assembly to move the first jaw member from the first position to the second position.

According to one embodiment of the present disclosure, a method of conducting an electrosurgical procedure is provided. The method includes energizing a solenoid assembly operably coupled to a drive assembly, actuating the drive assembly to actuate an end effector including a first jaw member and a second jaw member, moving the first jaw member relative to the second jaw member from a first position in spaced relation to the second jaw member to a second position closer to the second jaw member to grasp tissue therebetween, and supplying electrosurgical energy to at least one of the first jaw member or the second jaw member to effect a tissue seal.

In one aspect, the method includes advancing a knife assembly in a distal direction along the longitudinal axis to cut tissue along the tissue seal.

In one aspect, the method includes energizing the solenoid assembly operably coupled to the knife assembly to advance the knife assembly.

BRIEF DESCRIPTION OF THE DRAWINGS

Various embodiments of the subject instrument are described herein with reference to the drawings wherein.

DETAILED DESCRIPTION

Figure 1:
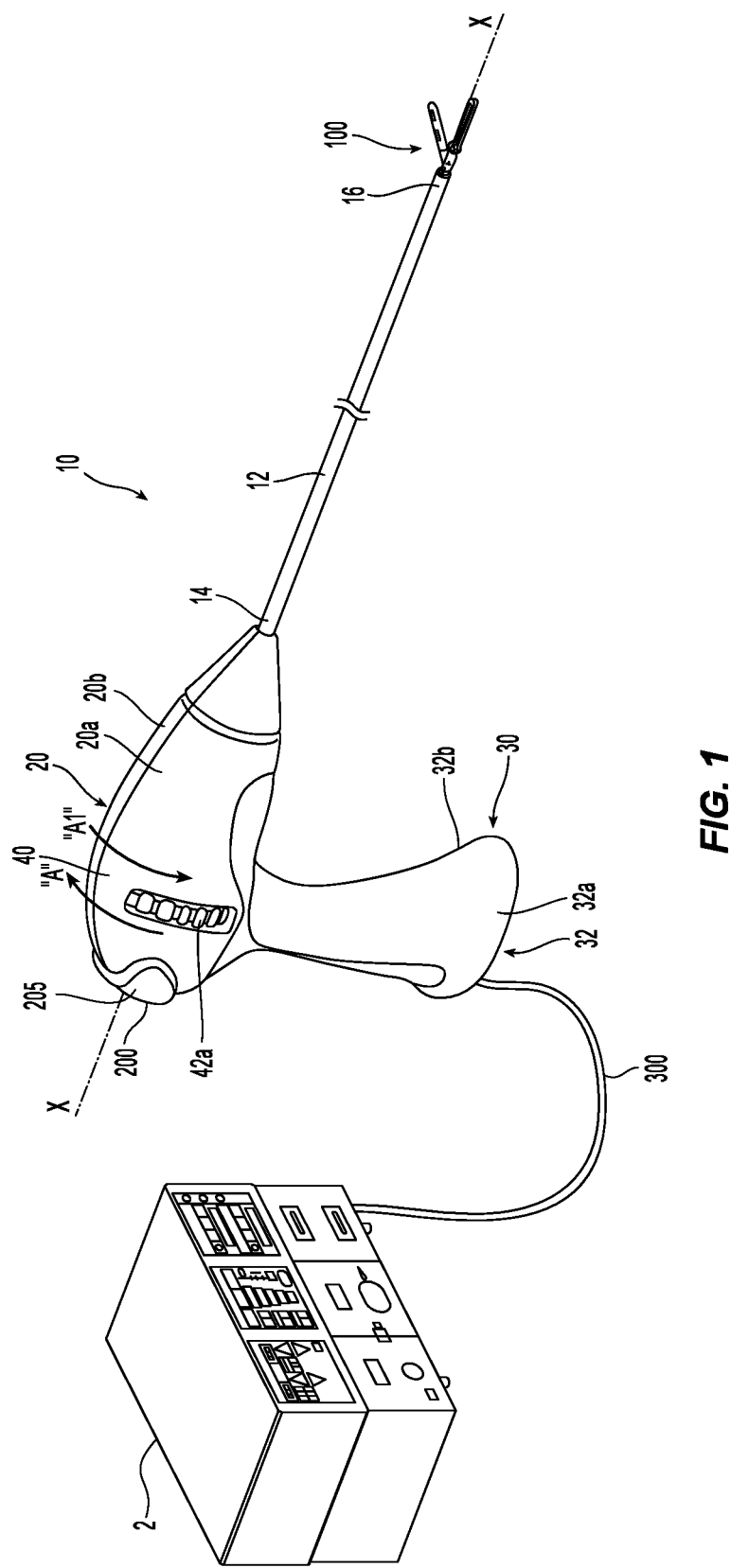
FIG. 1 is a perspective view of a surgical system with a bipolar forceps including a housing, a shaft, an end effector assembly, and a source of electrosurgical energy according to the present disclosure.

Embodiments of the presently disclosed surgical system, instruments, and methods are described in detail with reference to the drawings, in which like reference numerals designate identical or corresponding elements in each of the several views. As used herein, the term "distal" refers to that portion of the surgical instrument or components thereof, farther from the user, while the term "proximal" refers to that portion of the surgical or components thereof, closer to the user.

The present disclosure provides for a surgical instrument having one or more solenoids configured to actuate one or more corresponding drive shafts, which when actuated are moved longitudinally to, in turn, actuate an end effector. In embodiments, the end effector may include a pair of opposing jaw members and/or a knife assembly disposed between the jaw members. In further embodiments the jaw members may include electrodes configured to couple to a source of electrosurgical energy, e.g., an electrosurgical generator. In additional embodiments, the end effector may include a tissue fastener assembly and drive shaft is configured to approximate one of the jaw members (e.g., an anvil) relative to the other jaw member (e.g., cartridge assembly including a plurality of tissue fasteners). The solenoids may be powered by any suitable power source, such as a battery, which may be disposed within the surgical instrument, a DC rectifier, and the like. In embodiments, the power source may be coupled to the electrosurgical generator, which supplies electrosurgical energy to the end effector. The power source may be configured to rectify the current from the electrosurgical generator.

Figure 2:
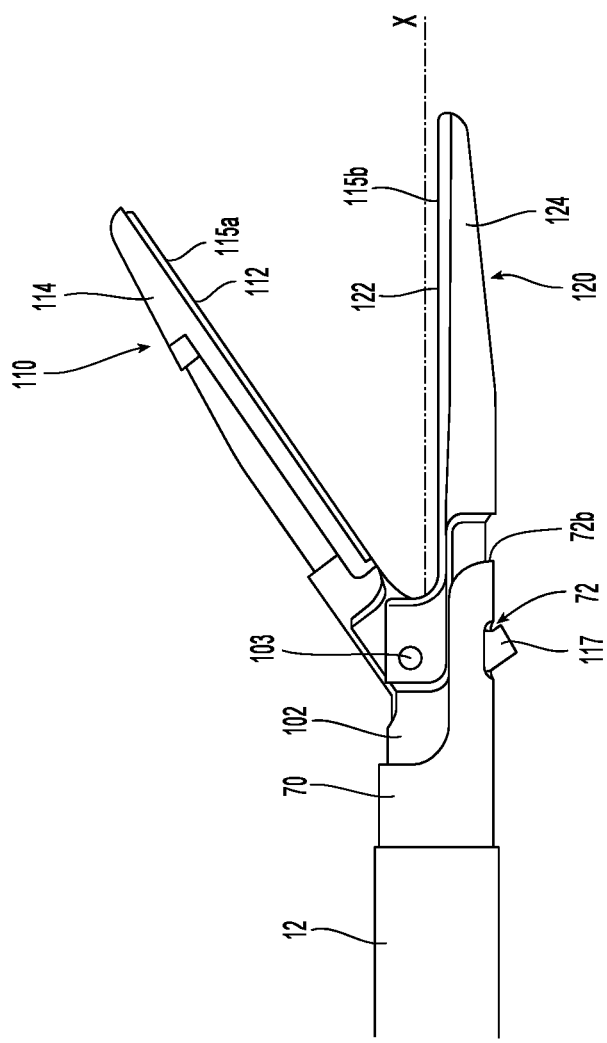
FIG. 2 is an enlarged, partial side view of the distal portion of an end effector assembly with jaw members shown in open configuration according to the present disclosure.
Figure 3:
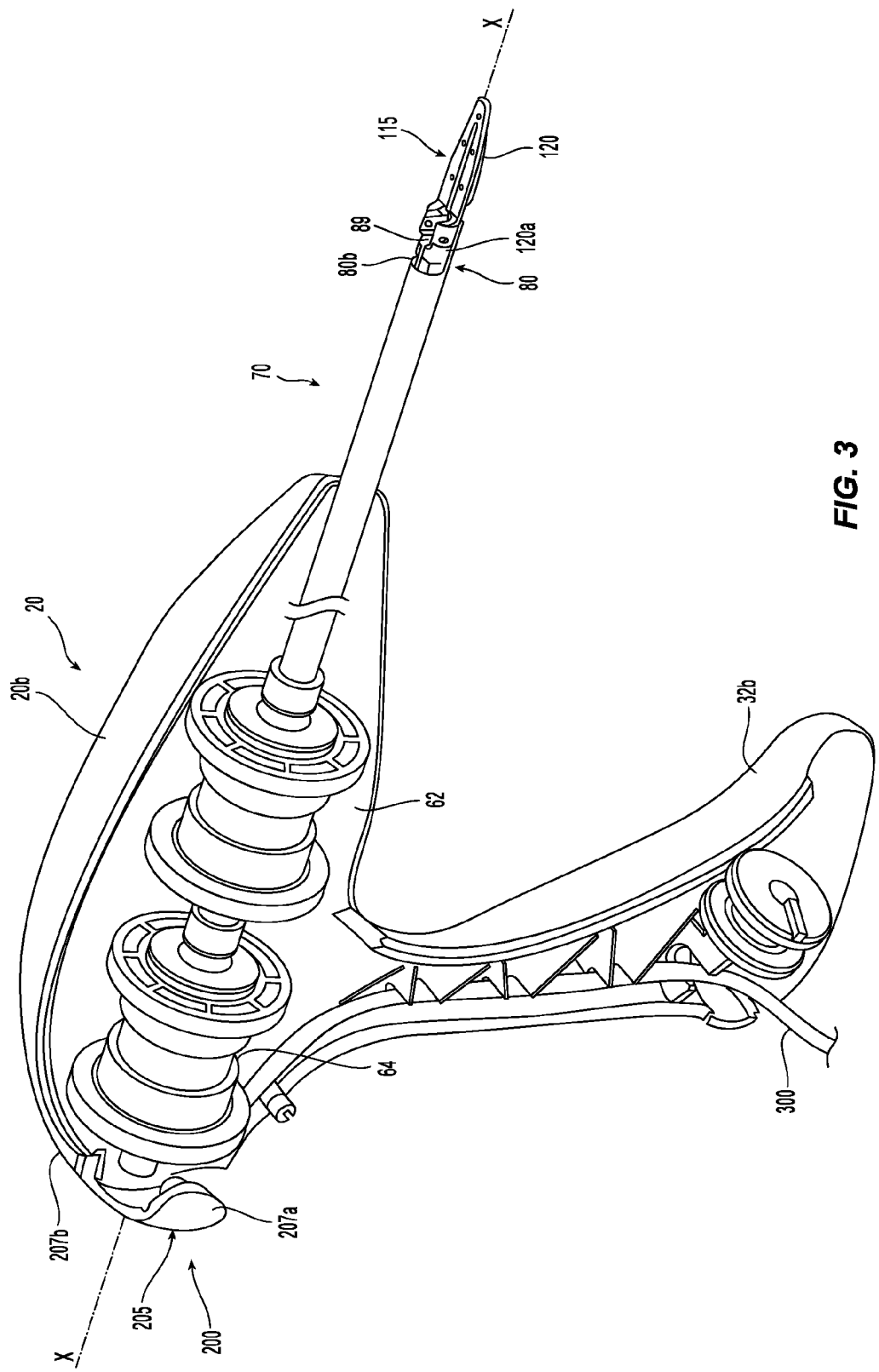
FIG. 3 is an enlarged, partial cutaway, perspective view of the bipolar forceps according to the present disclosure.

With reference to FIGS. 1-3, one embodiment of a forceps 10 is shown for use with various surgical procedures and generally includes a housing 20, a handle assembly 30, a rotating assembly 40, a drive assembly 50, a solenoid assembly 60, and an end effector assembly 100 which mutually cooperate to grasp, seal and divide tissue. Although the majority of the figure drawings depict the forceps 10 for use in connection with endoscopic surgical procedures, the present disclosure may be used with any mechanically actuated surgical device as described above.

The forceps 10 includes an elongated member such as, for example, a shaft 12 which has a distal end 16 dimensioned to mechanically engage the end effector assembly 100 and a proximal end 14 which mechanically engages the housing 20. The details of how the shaft 12 connects to the end effector assembly 100 are described below with respect to FIG. 2. The proximal end 14 of the shaft 12 is received within the housing 20. In the drawings and in the descriptions which follow, the term "proximal," as is traditional, will refer to the end of the forceps 10 which is closer to the user, while the term "distal" will refer to the end which is further from the user.

As best seen in FIG. 1, the forceps 10 also includes an electrosurgical cable 300, which connects the forceps 10 to a source of electrosurgical energy, e.g., a generator 2. Together, the forceps 10 and the generator 2 form a surgical system In embodiments, the generator 2 may include various safety and control features including isolated output, independent activation of surgical devices, and the like. The generator 2 may include a feedback system to sense changes in tissue and adjust voltage and current to maintain appropriate power. The cable 300 may include a plurality of wire leads, each of which transmit electrosurgical energy through their respective feed paths through the forceps 10 to the end effector assembly 100 as well as electrical energy to the solenoid assembly 60 addressed in more detail below with respect to FIGS. 3-6.

The handle assembly 30 includes a fixed handle 32, which may be integrally associated with the housing 20. As best seen in FIG. 1, the housing 20 may be formed from two housing halves 20a and 20b, each of which may include a plurality of interfaces (not shown) dimensioned to mechanically align and engage one another to form the housing 20 and the fixed handle 32 to enclose the internal working components of the forceps 10.

Figure 4:
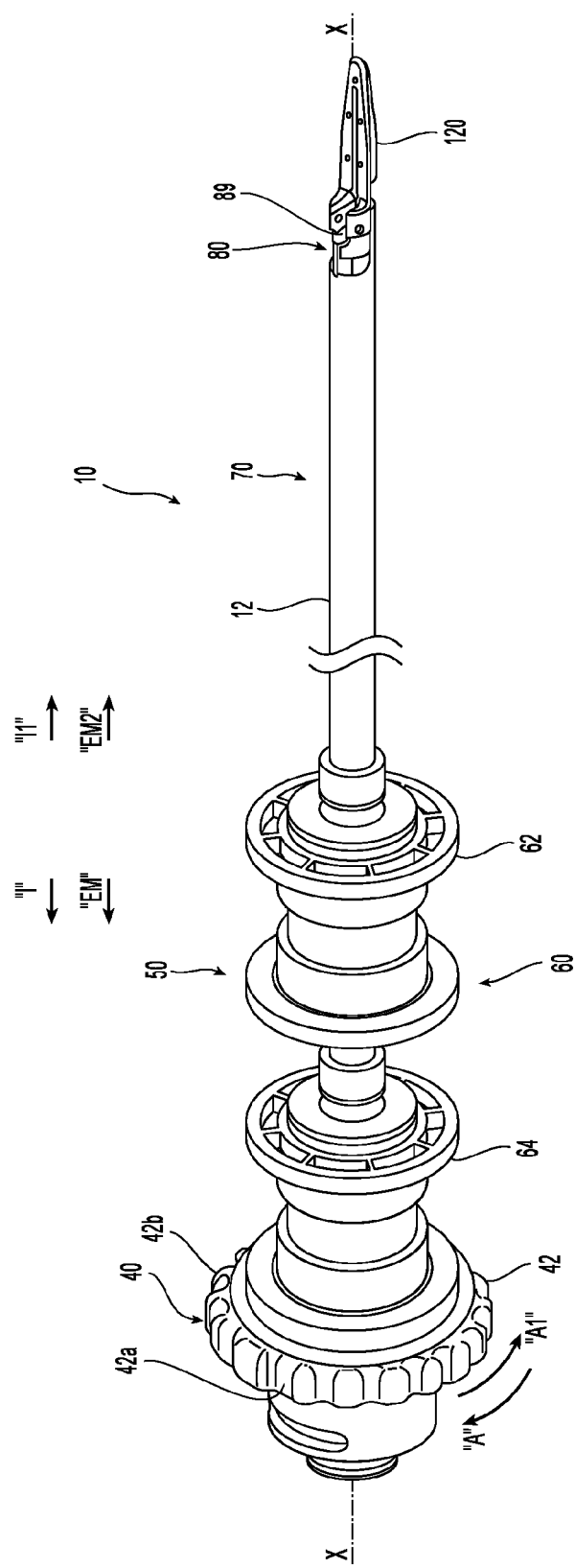
FIG. 4 is a perspective view of a rotating assembly, a drive assembly, and a solenoid assembly of the bipolar forceps according to the present disclosure.

The rotating assembly 40 is associated with the housing 20 and is rotatable in either direction provided by "A" or "A1" about a longitudinal axis "X-X" (see FIGS. 1 and 4).

Figure 6:
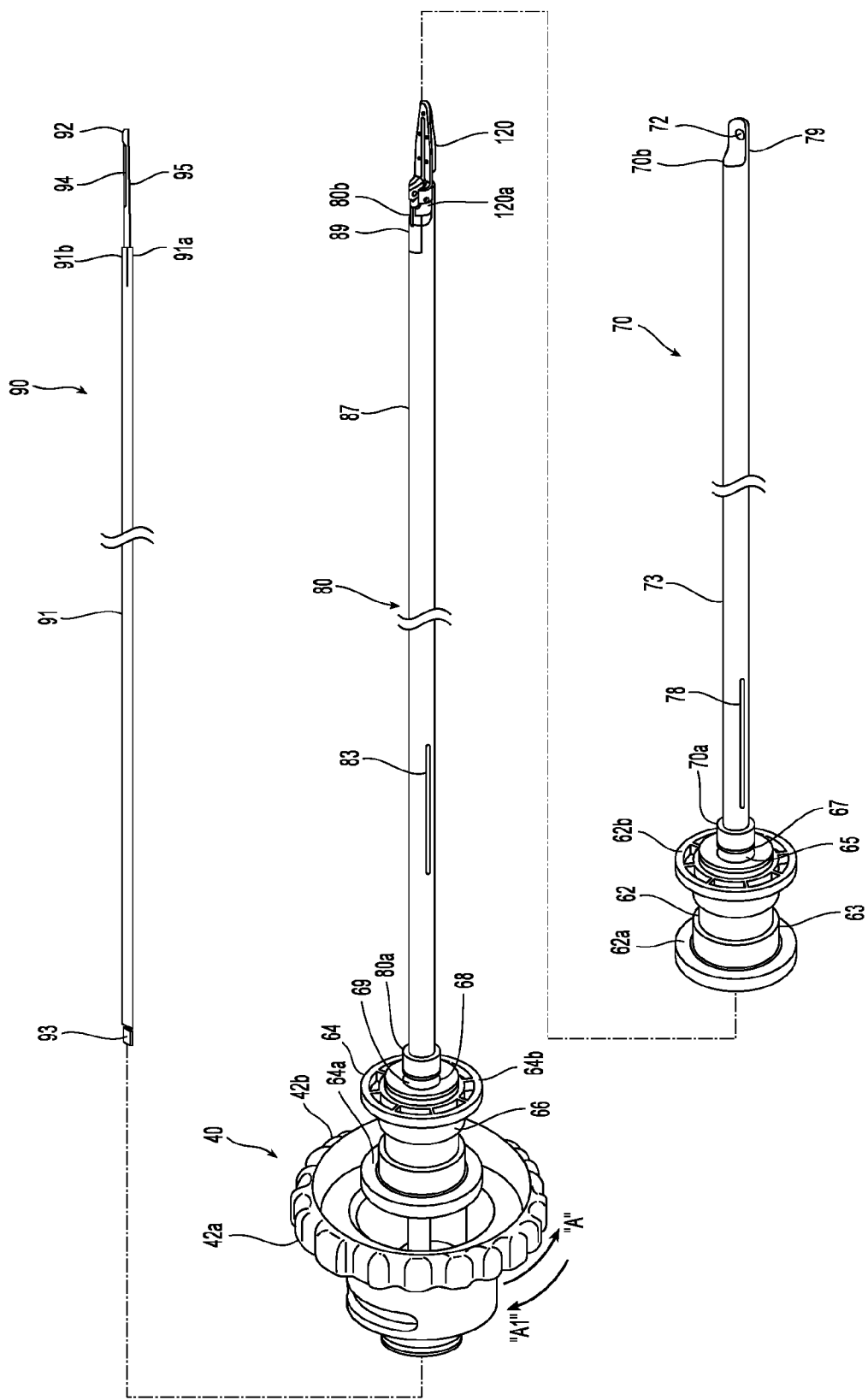
FIG. 6 is an enlarged perspective view with parts separated, which shows the knife assembly, the rotating assembly, the solenoid assembly, and the drive assembly of FIG. 4 according to the present disclosure.

Details of the rotating assembly 40 are described in more detail with respect to FIGS. 4 and 6. The rotating assembly 40 includes two halves, a first rotating half 42a and a second rotating half 42b. When assembled about a rotating tube 80, the first and second rotating halves, 42a and 42b, form the rotating assembly 40 which, in turn, houses the drive assembly 50 (see FIGS. 4 and 6). The rotating halves 42a and 42b include a series of detents/flanges (not shown), which are dimensioned to engage a pair of corresponding sockets or other mechanical interfaces (not shown) disposed within the rotating assembly 40.

The end effector assembly 100 includes a first jaw member 110 and a second jaw member 120. The first and second jaw members 110 and 120 may be opened, closed, and rotated to manipulate tissue. This enables the user to position and re-position the forceps 10 prior to activation and sealing. As illustrated in FIG. 1, the end effector assembly 100 is rotatable about the longitudinal axis "X-X" through rotation of the rotating assembly 40 in the direction "A" or "A1". As explained in more detail below, it is envisioned that the unique feed path of the cable lead (not shown) through the rotating assembly 40, along the shaft 12, and ultimately to the first and second jaw members 110 and 120, enables the user to rotate the end effector assembly 100 about 180 degrees in both the clockwise and counterclockwise direction without tangling or causing undue strain on the cable lead (not shown). The cable lead (not shown) is fused or clipped to the proximal end of the rotating tube 80 and is generally unaffected by rotation of the first and second jaw members 110 and 120. As can be appreciated, this facilitates the grasping and manipulation of tissue.

As shown in FIG. 1, a switch assembly 200 is activatable to energize the solenoid assembly 60, which is in turn operatively coupled to the drive assembly 50. The solenoid assembly 60 and the drive assembly 50 electromechanically cooperate to impart movement of the first and second jaw members 110 and 120 from an open position wherein the first and second jaw members 110 and 120 are disposed in spaced relation relative to one another, to a clamping or closed position wherein the first and second jaw members 110 and 120 cooperate to grasp tissue therebetween.

It is envisioned that the forceps 10 may be designed such that it is fully or partially disposable depending upon a particular purpose or to achieve a particular result. In embodiments, the end effector assembly 100 may be selectively and releasably engageable with the distal end 16 of the shaft 12 and/or the proximal end 14 of the shaft 12 may be selectively and releasably engageable with the housing 20 and the handle assembly 30. A replacement end effector assembly 100 or end effector assembly 100 and shaft 12 may be used to replace the old end effector assembly 100 as needed.

With continued reference to FIGS. 1-6, the end effector assembly 100 may be configured as a unilateral assembly in which the second jaw member 120 is fixed relative to the shaft 12. In this embodiment, the first jaw member 110 pivots about a pivot pin 103 relative to the shaft 12 to grasp tissue. In alternative embodiments, the end effector assembly 100 may be a bilateral assembly in which both of the first and second jaw members 110 and 120 may be pivotable relative to each other.

With reference to FIG. 2, the end effector assembly 100 includes the second jaw member 120 mounted in fixed relation to the shaft 12, and the first jaw member 110 mounted pivotably about the pivot pin 103 attached to the stationary jaw member 120. A reciprocating sleeve 70 is slidingly disposed within the shaft 12 and is remotely operable by the solenoid assembly 60. The first jaw member 110 includes a detent or protrusion 117 which extends from the first jaw member 110 through an aperture 72 disposed within the reciprocating sleeve 70 (FIG. 2). The first jaw member 110 is pivotably actuated by sliding the reciprocating sleeve 70 axially within the shaft 12 such that a distal end (not shown) of the aperture 72 abuts against the detent 117 on the first jaw member 110. Pulling the reciprocating sleeve 70 proximally closes the first and second jaw members 110 and 120 about tissue grasped therebetween and pushing the reciprocating sleeve 70 distally opens the first and second jaw members 110 and 120 for grasping purposes.

With reference to FIGS. 2-4, a knife channel 115 includes half channels 115a and 115b, each of which are longitudinally disposed through the first and second jaw members 110 and 120, respectively. As such, the knife assembly 90 can cut the tissue grasped between the first and second jaw members 110 and 120 when the first and second jaw members 110 and 120 are in a closed position. The knife assembly 90 is advanced through the tissue when the first and second jaw members 110 and 120 are closed, thus preventing accidental or premature activation of the knife assembly 90 through the tissue. The knife channel 115 is blocked when the first and second jaws members 110 and 120 are opened. However, when the first and second jaw members 110 and 120 are closed, the knife channel 115 is aligned for activation. It is envisioned that the half channel 115a, disposed on the first jaw member 110, cooperates with the corresponding half channel 115b disposed on the second stationary jaw member 120 to facilitate the longitudinal extension of the knife assembly 90 along a cutting plane to separate the tissue along the formed tissue seal.

With reference to FIG. 2, each of the first and second jaw members 110 and 120 includes an insulative jaw housing 114 and 124, respectively, having a conductive surface 112 and 122, disposed thereon. The conductive surfaces 112 and 122 are coupled to the generator 2. The conductive surfaces 112 and 122 are configured to transmit electrosurgical energy from the generator 2 to seal tissue that is grasped between the jaw members 110 and 120.

In embodiments, the end effector assembly 100 may be structured such that electrical energy can be routed through the reciprocating sleeve 70 at the detent 117 contact point with the reciprocating sleeve 70 to energize the conductive surfaces 112 and 122. It is further contemplated that a "brush" or lever (not shown) may be used to contact the back of the first jaw member 110 when the first jaw member 110 closes. In this instance, the electrical energy would be routed through the detent 117 to the second jaw member 120. Alternatively, the cable 300 leads (not shown) may be routed to energize the second jaw member 120 and the other electrical potential may be conducted through the reciprocating sleeve 70 and transferred to the first jaw member 110, which establishes electrical continuity upon retraction of the reciprocating sleeve 70.

The second jaw member 120 is coupled to a distal end 80b of the rotating tube 80, which is coupled to the rotating assembly 40 such that rotation of the rotating assembly 40 will impart rotation to the second jaw member 120 of the end effector assembly 100. As described above, the conductive surface 122 of the second jaw member 120 is connected to a second electrical potential through the rotating tube 80 which is connected at its proximal end 80a to an electrical lead. The second jaw member 120 may be welded to the rotating tube 80 and may include a fuse clip, spring clip or other electro-mechanical connection, which provides electrical continuity to the second jaw member 120 from the electrical lead.

With reference to FIG. 6, the rotating tube 80 includes an elongated guide slot 87 disposed in an upper portion thereof which is dimensioned to carry an electrical lead (not shown) therealong. A first lead (not shown) carries a first electrical potential to the conductive surface 112 of the first jaw member 110. Similarly, a second lead (not shown) is conducted through the rotating tube 80 to the conductive surface 122 of the second jaw member 120 to carry the second electrical potential. In embodiments, an electrical lead may be coupled directly to the conductive surface 122.

Figure 5:
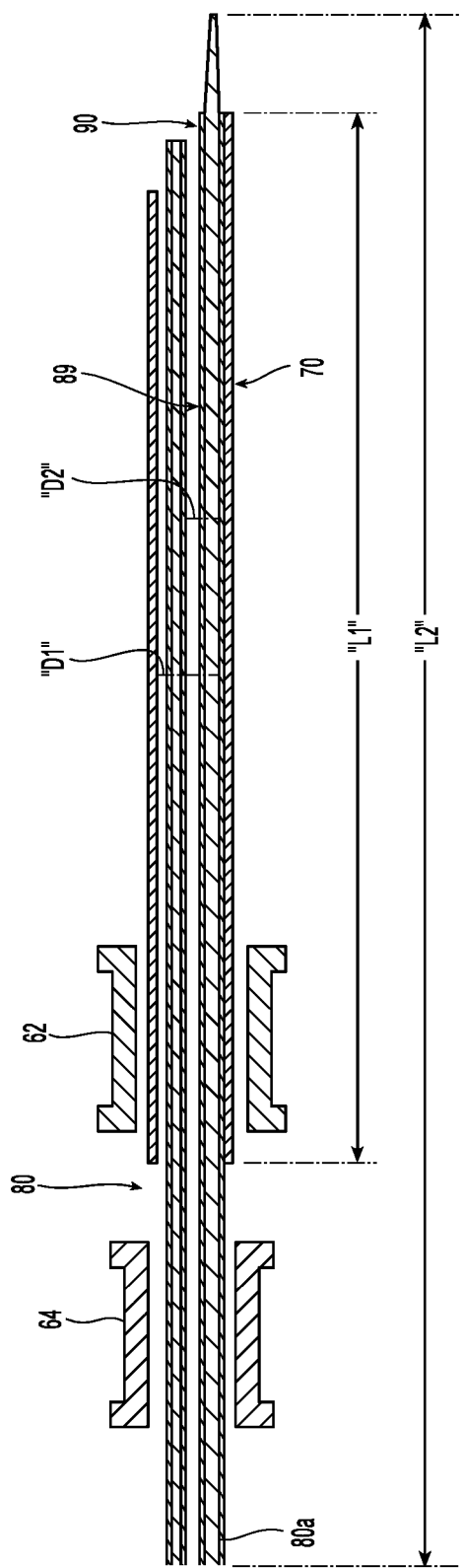
FIG. 5 is a cross-sectional view of the drive assembly and the solenoid assembly of FIG. 4 according to the present disclosure.

With reference to FIGS. 4-6, the drive assembly 50 includes the solenoid assembly 60, the reciprocating sleeve 70, the rotating tube 80, and the knife assembly 90. More particularly, the reciprocating sleeve 70 includes a distal end 70b which includes the aperture 72 formed therein for actuating the detent 117 of the first jaw member 110. The distal end 70b of the reciprocating sleeve 70 includes a scoop-like support member 79 for supporting a proximal end 120a of the fixed jaw member 120 therein. A proximal end 70a of the reciprocating sleeve 70 includes a slot 78 defined therein which is dimensioned to slidingly support the knife assembly 90 for longitudinal reciprocation thereof to sever tissue. The slot 78 also permits retraction of the reciprocating sleeve 70 over the knife assembly 90 during the closing of the first jaw member 110 relative to the second jaw member 120. The proximal end 70a of the reciprocating sleeve 70 is positioned within an aperture 67 in a first solenoid 62 of the solenoid assembly 60 to permit selective reciprocation thereof upon activation of the solenoid assembly 60, the details of which are discussed below.

As shown in FIGS. 3-6, the distal end 80b of the rotating tube 80 is configured for receiving the proximal end 120a of the second jaw member 120. The rotating tube 80 includes a channel 89 (FIG. 5) defined therethrough which houses the knife assembly 90, which reciprocates upon distal activation thereof along an elongated guide rail 83 which guides the knife assembly 90. The proximal end 80a of the rotating tube 80 includes a laterally oriented slot (not shown), which is designed to interface with the rotating assembly 40.

As addressed above, and with reference to FIGS. 3-6, the solenoid assembly 60 is disposed within the housing 20 and is operably coupled to the drive assembly 50. Similar to the first solenoid 62, in some embodiments, the solenoid assembly 60 includes a second solenoid 64. It is contemplated that the solenoid assembly 60 may include any number of solenoids, e.g., one solenoid or more than two solenoids. In embodiments where the solenoid assembly 60 includes two solenoids, the first solenoid 62 is operatively coupled to the reciprocating sleeve 70 and the second solenoid 64 is operatively coupled to the rotating tube 80.

First solenoid 62 includes a cylindrical cross-section and extends along the longitudinal axis "X-X" between a proximal end 62a and a distal end 62b. The first solenoid 62 includes an outer surface 63 and an inner surface 65. The inner surface 65 defines the aperture 67 extending therethrough between the proximal end 62a and the distal end 62b. As described above, the first solenoid 62 is coupled with the reciprocating sleeve 70. A portion of the reciprocating sleeve 70 is disposed within the aperture 67 such that the inner surface 65 of the first solenoid 62 is in communication with an outer surface 73 of the reciprocating sleeve 70. In embodiments, the reciprocating sleeve 70 may be frictionally disposed within the aperture 67, wherein the coefficient of friction is "F1". It is contemplated that the reciprocating sleeve 70 is formed from a ferromagnetic material. In alternative embodiments, it is contemplated that a ferrous alloy can be deposited onto the reciprocating sleeve 70.

The second solenoid 64, similar to the first solenoid 62 also includes a cylindrical cross-section and extends along the longitudinal axis "X-X" between a proximal end 64a and a distal end 64b. The second solenoid 64 is located proximally of the first solenoid 62. The second solenoid 64 includes an outer surface 66 and an inner surface 68. The inner surface 68 defines an aperture 69 extending therethrough between the proximal end 64a and the distal end 64b. The rotating tube 80 is disposed within the aperture 69 such that the inner surface 68 of the second solenoid 64 is in communication with an outer surface 86 of the rotating tube 80. The rotating tube 80 is formed from a non-ferrous material such that it is not susceptible to magnetic fields generated by the first and second solenoids 62 and 64.

With respect to FIG. 5, the reciprocating sleeve 70 has a length "L1" and the rotating tube 80 has a length "L2", where "L2" is greater than "L1". Further, as seen in FIG. 5, the reciprocating sleeve 70 does not extend past the second solenoid 64. The reciprocating sleeve 70 has an inner surface 75 defining a channel 77 extending through the length "L1". Similarly, the rotating tube 80 has an inner surface 88 defining the channel 89 extending through the length "L2". The channel 77 of the reciprocating sleeve 70 has a diameter "D1" and the channel 89 of the rotating tube 80 has a diameter "D2", wherein "D1" is greater than "D2", such that the rotating tube 80 is capable of being disposed within the channel 77 of the reciprocating sleeve 70, as shown in FIG. 5. As also seen in FIG. 5, the knife assembly 90 is disposed within the channel 89 of the rotating tube 80. The knife assembly 90 includes an elongated rod 91 having a bifurcated distal end including prongs 91a and 91b which cooperate to receive a knife bar 94 therein. The knife assembly 90 also includes a proximal end 93 which is keyed to facilitate insertion into the rotating tube 80.

The knife bar 94 includes a series of steps 96a, 96b and 96c which reduce the profile of the knife bar 94 towards the distal end 95 thereof. The distal end 95 of the knife bar 94 includes a knife support (not shown) which is dimensioned to retain the knife assembly 90. Similar to the reciprocating sleeve 70, the knife assembly 90 may be formed from a ferromagnetic material. In alternative embodiments, it is contemplated that a ferrous alloy can be deposited onto the knife assembly 90.

The assembled solenoid assembly 60 coupled with the drive assembly 50 is best shown in FIG. 4. As discussed above, the reciprocating sleeve 70 is partially disposed within the aperture 67 of the first solenoid 62. Similarly, the rotating tube 80 is partially disposed within the aperture 69 of the second solenoid 64. Further, as shown in FIGS. 4 and 6, the reciprocating sleeve 70 houses the rotating tube 80, and the knife assembly 90 is disposed within the rotating tube 80.

In operation, when the first solenoid 62 is energized, the current flows distally as shown by the arrow represented by "I1". This flow of current creates a magnetic field within the first solenoid 62 in the proximal direction shown by the arrow represented by "EM". As a result of this magnetic field, the reciprocating sleeve 70 is translated proximally along the longitudinal axis "X-X" relative to the first solenoid 62. The translation of the reciprocating sleeve 70 in this direction imparts a pulling force on the detent 117, causing the first and second jaw members 110 and 120 to close.

Once the first and second jaw members 110 and 120 are closed, the second solenoid 64 may be energized to advance the knife assembly 90. Similar to the first solenoid 62, there is a current that is applied to the second solenoid 64. However, the current in the second solenoid is applied in the proximal direction shown by the arrow "I". This flow of current creates a magnetic field within the second solenoid 64 in the distal direction shown by the arrow given by "EM2". Due to the ferromagnetic coating on the knife assembly 90, the knife assembly 90 is deployed in the direction of the magnetic field. In this embodiment, the knife assembly 90 is translated along the longitudinal axis "X-X" distally relative to the second solenoid 64. Since the rotation tube 80 is formed from a non-ferrous material it is unaffected by the magnetic field and is not moved longitudinally.

In order to open the first and second jaw members 110 and 120, and retract the knife assembly 90, the current supplied to the first and second solenoids 62 and 64 are reversed. In particular, it is contemplated that a current is applied to the first solenoid 62 in the proximal direction represented by arrow "I" whereas a current is applied to the second solenoid 64 in the distal direction represented by arrow "I1". As noted, this will impose a magnetic field within the solenoids 62 and 64 in a direction opposite that of the current flow. The magnetic field will in turn impose a force on the ferromagnetic coating of the reciprocating sleeve 70 and the knife assembly 90, forcing both to translate along the longitudinal axis "X-X" in the direction of the magnetic field.

Alternatively, it is contemplated that there may be a biasing member (not shown) coupled to the pivot pin 103 of the end effector assembly 100. In this embodiment, it is contemplated that the biasing member provides a spring bias for spacing apart the first and second jaw members 110 and 120. As such, when the reciprocating sleeve 70 is not translated in the proximal direction, the first and second jaw members 110 and 120 are biased to stay open. Similarly, the knife assembly 90 may also include a biasing member to return the knife assembly 90 to its retracted position after it is advanced to cut tissue.

With reference to FIGS. 1 and 3, the forceps 10 includes the switch assembly 200 for controlling operation of the forceps 10 including opening and closing of the first and second jaw members 110 and 120, reciprocation of the knife assembly 90, and supplying energy to the conductive surfaces 112 and 122. The switch assembly 200 may be any suitable switch and may include an ergonomically dimensioned toggle plate 205 having a pair of wings 207a and 207b which conform to the outer shape of the housing 20. It is envisioned that the switch assembly 200 permits the user to selectively activate the forceps 10 in a variety of different configurations. The switch assembly 200 may be coupled to various timer and control logic circuits (e.g., controller) configured to provide for sequential operation of the solenoid assembly 60 and activation of electrosurgical energy. In one embodiment, it is contemplated that the wing 207a may provide current flow in a first direction to close the first and second jaw members 110 and 120, active electrosurgical energy, and advance the knife assembly 90. Whereas, the wing 207b may provide current flow in a second opposite direction to retract the knife assembly 90 and open the first and second jaw members 110 and 120. The electrical leads of the cable 300 are electrically connected to an electrical interface (not shown) on the switch assembly 200.

When the switch assembly 200 is depressed, electrosurgical energy is also transferred to the first and second jaw members 110 and 120. It is envisioned that a safety switch or circuit (not shown) may be employed such that the electrosurgical energy is not transmitted unless the first and second jaw members 110 and 120 are closed and/or unless the first and second jaw members 110 and 120 have tissue held therebetween. In the latter instance, a sensor may be employed to determine if tissue is held therebetween. In addition, other sensor mechanisms may be employed which determine pre-surgical, concurrent surgical (i.e., during surgery) and/or post-surgical conditions. The sensor mechanisms may also be utilized with a closed-loop feedback system coupled to the generator 2 to regulate the electrosurgical energy based upon one or more pre-surgical, concurrent surgical or post-surgical conditions.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:
1. A surgical instrument, comprising:
a housing;
an elongated member extending distally from the housing and defining a longitudinal axis;
an end effector assembly coupled to a distal end of the elongated member, the end effector assembly including a first jaw member and an opposing second jaw member, the first jaw member moveable relative to the second jaw member from a first position in spaced relation to the second jaw member to a second position closer to the second jaw member to grasp tissue therebetween, at least one of the jaw members adapted to connect to an electrosurgical energy source such that the jaw members are capable of conducting electrosurgical energy through tissue grasped therebetween to effect a tissue seal;
a drive assembly disposed within the elongated member and including a reciprocating sleeve operably coupled to the end effector and configured to move the first jaw member from the first position to the second position;
a knife assembly movably disposed within the reciprocating sleeve;
a solenoid assembly disposed within the housing, the solenoid assembly including a first solenoid positioned about the reciprocating sleeve and a second solenoid positioned about the knife assembly, the solenoid assembly adapted to connect to a power source; and
a switch assembly connected to the housing, the switch assembly activatable to energize the solenoid assembly such that the first solenoid moves the reciprocating sleeve along the longitudinal axis relative thereto, to transition the first jaw member from the first position to the second position.
2. The surgical instrument of claim 1, wherein the knife assembly is movably disposed between the first jaw member and the second jaw member.

3. The surgical instrument of claim 2, wherein the second solenoid of the solenoid assembly is configured to actuate the knife assembly, the knife assembly being movable after the first jaw member is actuated from the first position to the second position.

4. The surgical instrument of claim 1, wherein the switch assembly is configured to selectively supply electrosurgical energy to the first and second jaw members to effect the tissue seal.

5. The surgical instrument of claim 1, wherein the first jaw member is configured to couple to a first electrical potential and the second jaw member is configured to couple to a second electrical potential.

6. The surgical instrument of claim 1, wherein at least one of the reciprocating sleeve or the knife assembly includes a ferromagnetic material.

7. A surgical system comprising:
   an electrosurgical generator, including an RF output stage configured to generate electrosurgical energy; and
   a surgical instrument including:
      a housing;
      an elongated member extending distally from the housing and defining a longitudinal axis;
      an end effector assembly coupled to a distal end of the elongated member, the end effector assembly including a first jaw member and an opposing second jaw member, the first jaw member moveable relative to the second jaw member from a first position in spaced relation to the second jaw member to a second position closer to the second jaw member to grasp tissue therebetween, at least one of the jaw members adapted to connect to an electrosurgical energy source such that the jaw members are capable of conducting the electrosurgical energy through tissue grasped therebetween to effect a tissue seal;
      a drive assembly disposed within the elongated member and including a reciprocating sleeve operably coupled to the end effector and configured to move the first jaw member from the first position to the second position;
      a knife assembly movably disposed within the reciprocating sleeve;
      a solenoid assembly disposed within the housing, the solenoid assembly including a first solenoid positioned about the reciprocating sleeve and a second solenoid positioned about the knife assembly, the solenoid assembly adapted to connect to a power source; and
      a switch assembly connected to the housing, the switch assembly activatable to energize the solenoid assembly such that the first solenoid moves the reciprocating sleeve along the longitudinal axis relative thereto, to transition the first jaw member from the first position to the second position.

8. The surgical system of claim 7, wherein the knife assembly is movably disposed between the first jaw member and the second jaw member.

9. The surgical system of claim 8, wherein the second solenoid of the solenoid assembly is configured to actuate the knife assembly, the knife assembly being movable after the first jaw member is actuated from the first position to the second position.

10. The surgical system of claim 7, wherein the switch assembly is configured to selectively supply electrosurgical energy to the first and second jaw members to affect the tissue seal.

11. The surgical system of claim 7, wherein the first jaw is configured to couple to a first electrical potential and the second jaw is configured to couple to a second electrical potential.

12. The surgical instrument of claim 7, wherein at least one of the reciprocating sleeve or the knife assembly includes a ferromagnetic material.

13. A method of conducting an electrosurgical procedure, the method comprising:
   energizing a first solenoid of a solenoid assembly including the first solenoid and a second solenoid, the first solenoid disposed about a reciprocating sleeve of a drive assembly and the second solenoid disposed about a knife assembly;
   actuating the drive assembly to actuate the reciprocating sleeve, the reciprocating sleeve operably coupled an end effector including a first jaw and a second jaw;
   moving the reciprocating sleeve along a longitudinal axis relative to the first solenoid and engaging the end effector to move the first jaw relative to the second jaw from a first position in spaced relation to the second jaw to a second position closer to the second jaw to grasp tissue therebetween; and
   supplying electrosurgical energy to at least one of the first jaw or the second jaw to effect a tissue seal.

14. The method of claim 13, further comprising:
   energizing the second solenoid of the solenoid assembly operably coupled to the knife assembly to advance the knife assembly.

15. The method of claim 14, advancing the knife assembly in a distal direction along the longitudinal axis to cut tissue along the tissue seal.

* * * * *